United States Patent [19]

Holtkamp

[11] Patent Number: Plant 5,615

[45] Date of Patent: Dec. 31, 1985

[54] AFRICAN VIOLET PLANT NAMED MIAMI

[75] Inventor: Reinhold Holtkamp, Isselburg, Fed. Rep. of Germany

[73] Assignee: Gessellschaftsvertrag uber die Ergindergemeinschaft "Optimara", Fed. Rep. of Germany

[21] Appl. No.: 568,447

[22] Filed: Jan. 5, 1984

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of African violet plant named Miami characterized by its vigorous growth habit, girl-type leaves which are heaving indented and serrated, 7–9 upright flower stems each of which carries 5–9 flowers which are intensive pink and two-tone in color, with the center of the flower being darker, and by its profuse flowering habit.

1 Drawing Figure

The present invention comprises a new and distinct cultivar of African violet plant, botanically known as *Saintpaulia ionantha,* and named Miami.

The new cultivar was referred to during the breeding and selection process by the designation G 9/18, and is a product of a planned breeding program.

The new cultivar was originated from a cross made in a controlled breeding program in Isselburg, West Germany. The female, or seed parent was a cultivar designated D 150/2 Red Girl. The male, or pollen parent was a cultivar designated D 134/11 Lilac Frilled.

The new cultivar Miami was discovered and selected by me as a flowering plant within the progeny of the stated cross in a controlled environment in Isselburg, West Germany. Asexual reproduction of the new cultivar by leaf cuttings and by divison of shoots, as performed by me at Isselburg, West Germany, has demonstrated that the combination of characteristics as herein disclosed for the new cultivar are firmly fixed and are retained through successive generations of asexual reproduction.

Miami has not been observed under all possible environmental conditions. The phenotype may vary signficantly with variations in environment such as temperature, light intensity and day length. The following observations, measurements and values describe the new cultivar as grown in Isselburg, West Germany, and Nashville, Tenn. under greenhouse conditions which closely approximate those generally used in commercial practice.

The following traits have been repeatedly observed and are determined to be basic characteristics of Miami, which in combination distinguish this African violet as a new and distinct cultivar:

1. Vigorous growth habit.
2. Attractive shiny leaves with bright centers (girl type).
3. Leaves heavily indented and serrated.
4. Seven to nine upright flower stems.
5. Five to nine flowers per stem.
6. Intensive pink, two-tone flower color.
7. Center of flower is darker in color.
8. Profuse flowering habits.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values are taken under natural light conditions at approximately 3 P.M. on November 30 in Nashville, Tenn. When Miami is grown under cooler conditions, the flower color will be somewhat more intensive, and under relatively high finishing temperatures, the flower color will fade somewhat.

Botanical classification: *Saintpaulia ionantha,* Ramat cv MIAMI

Parentage:

*Male parent.*—D 134/11 Lilac frilled.

*Female parent.*—D 150/2 Red Girl.

Propagation: The new cultivar holds its distinguishing characteristics through successive propagations by leaf cuttings and by division of shoots.

Plant: From 7 cm. to 9 cm. tall when grown in pots, and approximately 20–23 cm. in diameter when fully grown.

*Leaves.*—General form: Round to heart-shape. Diameter: 60–65 mm. Texture: Leather-like. Aspect: Shiny, slightly hairy, indented. Veins: Well pronounced light green, shiny. Color (upperside): Yellow green, 147 between A-B. Color (underside): Yellow green 147D. Petiole: Brownish.

*Flowers.*—Buds: Ball shape, intensive red purple color. Sepals: 5, long and spear shape, and greenish brown in color. Calyx: Flat funnel. Peduncle: Wire-like.

*Individual flowers.*—Size: 40 mm. Color: Red purple, center slightly darker. Upperside: Red purple, Group 74 between C-D. Underside: Red purple, Group 74D. Borne: On upright wire-like petals. Shape: Violet shape. Flowering time: 12–13 weeks after potting.

*Reproductive organs.*—Anthers: 2 anthers composed by 4 cells. Filaments: Light green. Styles: Red purple glassy stigma.

*Roots.*—White when young and active; brownish when older.

*Disease resistance.*—Good as experienced to date.

General observations: Miami is a girl type variety with attractive dark green leaves which have a bright green center. There ar 7–9 wire-like flower stems each of which carries 9 and more single pink flowers, with an additional flower petal occasionally appearing in the center. The mature plant has a full flower head and is saleable 11–12 weeks after potting.

I claim:

1. A new and distinct cultivar of African violet plant named Miami, as described and illustrated, and particularly characterized by its vigorous growth habit, girl-type leaves which are heavily indented and serrated, 7–9 upright flower stems each of which carries 5–9 flowers which are intensive pink and two-tone in color, with the center of the flower being darker, and by its profuse flowering habit.

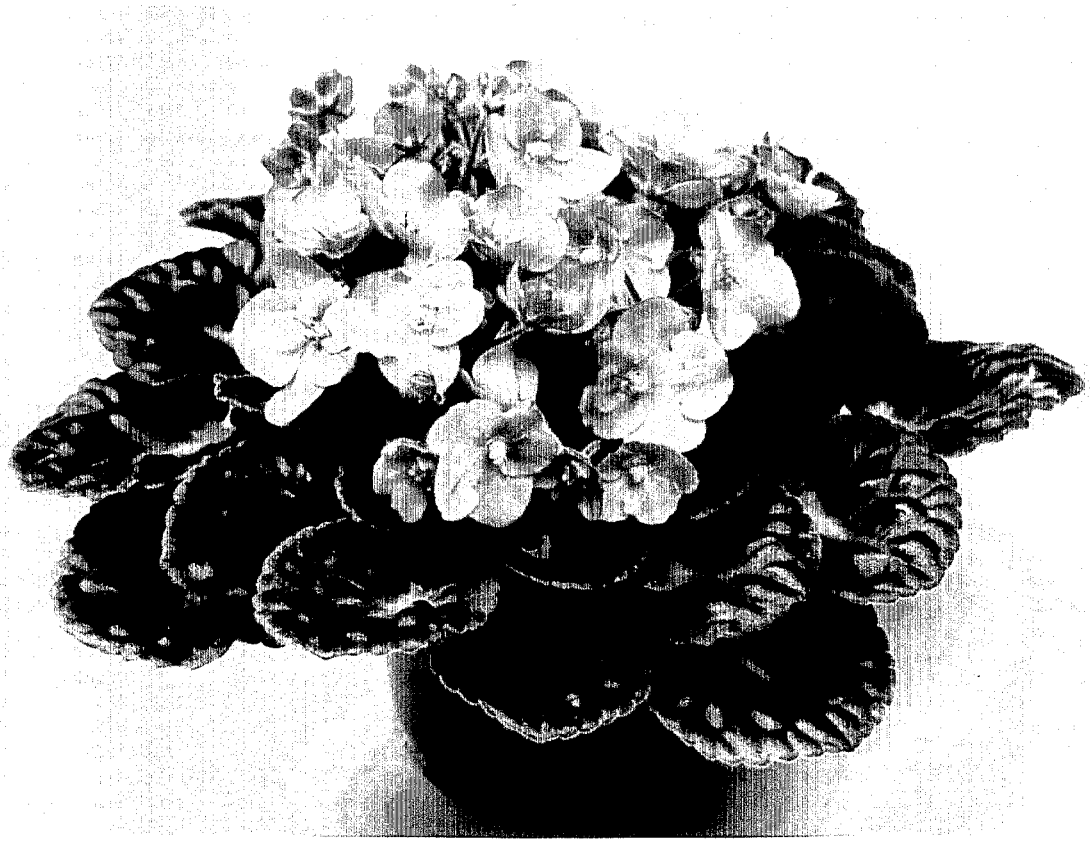

* * * * *